United States Patent [19]

Cole

[11] 4,196,613
[45] Apr. 8, 1980

[54] DEVICE FOR MEASURING THE FLUID DENSITY OF A TWO-PHASE MIXTURE

[75] Inventor: Jack H. Cole, Idaho Falls, Id.

[73] Assignee: The United States of America as represented by the United States Department of Energy, Washington, D.C.

[21] Appl. No.: 957,618

[22] Filed: Nov. 30, 1978

[51] Int. Cl.² .............................................. G01N 9/32
[52] U.S. Cl. .................................................. 73/32 R
[58] Field of Search .................... 73/32 R, 229, 231 R

[56] References Cited

U.S. PATENT DOCUMENTS

| 3,176,222 | 3/1965 | Atkisson | 73/32 R X |
| 3,298,221 | 1/1967 | Miller et al. | 73/32 R |
| 3,783,688 | 1/1974 | Knauth | 73/229 X |
| 3,958,447 | 5/1976 | Baker et al. | 73/32 R |

Primary Examiner—Gerald Goldberg
Assistant Examiner—Joseph W. Roskos
Attorney, Agent, or Firm—R. V. Lupo; Frank H. Jackson

[57] ABSTRACT

A device for measuring the fluid density of a two-phase mixture flowing through a tubular member. A rotor assembly is rotatively supported within the tubular member so that it can also move axially within the tubular member. The rotor assembly is balanced against a pair of springs which exert an axial force in the opposite direction upon the rotor assembly. As a two-phase mixture flows through the tubular member it contacts the rotor assembly causing it to rotate about its axis. The rotor assembly is forced against and partially compresses the springs. Means are provided to measure the rotational speed of the rotor assembly and the linear displacement of the rotor assembly. From these measurements the fluid density of the two-phase mixture is calculated.

15 Claims, 3 Drawing Figures

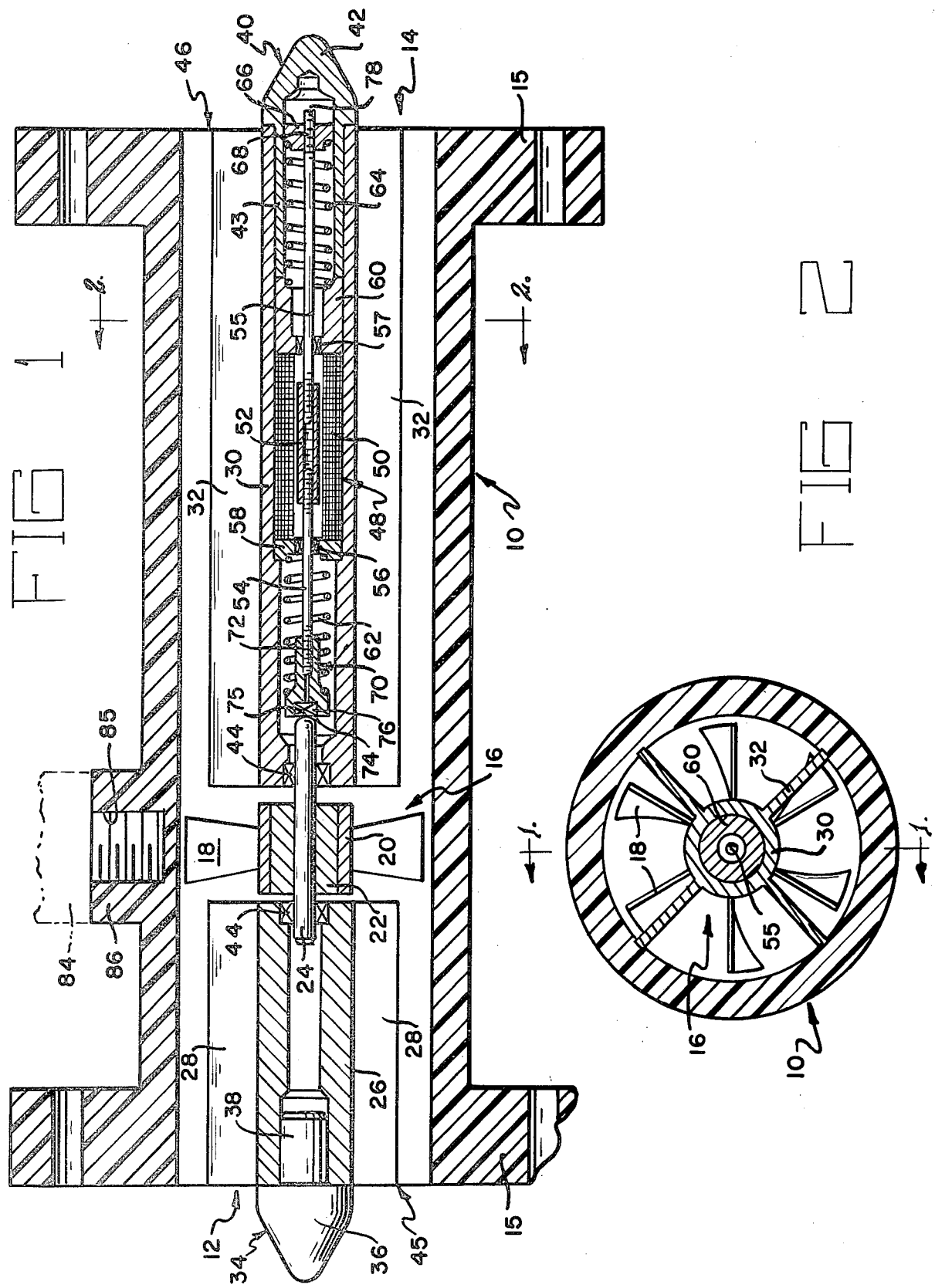

DEVICE FOR MEASURING THE FLUID DENSITY OF A TWO-PHASE MIXTURE

CONTRACTUAL ORIGIN OF THE INVENTION

The invention described herein was made in the course of, or under, a contract with the UNITED STATES DEPARTMENT OF ENERGY.

BACKGROUND OF THE INVENTION

This invention relates to a device for measuring the fluid density of a two-phase mixture flowing through a tube. With the increased emphasis on safety, designers of pressurized water nuclear reactors are seeking to develop instrumentation capable of accurately measuring both single-phase and two-phase flow. Measurement of two-phase flow is difficult because of rapidly changing fluid densities and flow regimes. This measurement is especially difficult in the harsh environment of a nuclear reactor system.

An instrument presently used to measure two-phase flow in nuclear reactors is a drag disk turbine transducer (DDT). The DDT consists of a spring mounted drag disk and a turbine rotor in series within a common shroud. A variable reluctance transducer senses drag disk deflection which is proportional to the fluid density multiplied by the fluid velocity squared. The rotor speed, which is directly proportional to fluid velocity is sensed by an eddy current transducer. Recorded data from the variable reluctance and eddy current transducers are correlated to yield a mass flow rate versus time which is the fluid density of the two-phase mixture or two-phase flow.

The DDT is designed to measure flow in both forward and reverse directions. During forward flow, the drag disk shadows the rotor, while during reverse flow the rotor shadows the drag disk. Because the drag disk and rotor are separated axially and all of the two-phase mixture that contacts the rotor does not contact the drag disk, there is concern about data correlation over all encountered flow regimes.

BRIEF SUMMARY OF THE INVENTION

This invention is directed to a device for measuring the fluid density of a two-phase mixture flowing through a tubular member. A rotor assembly is rotatively supported within the tubular member so that it can also move axially within the tubular member. The rotor assembly is balanced against a pair of springs which exert an axial force in the opposite direction upon the rotor assembly.

As a two-phase mixture flows through the tubular member, it contacts the rotor assembly, causing it to rotate about its axis. The rotor assembly is thereby forced against and partially compresses one of the springs. Means are provided to measure the rotational speed of the rotor assembly which is directly proportional to the velocity of the two-phase mixture. Means are also provided to measure the linear displacement of the rotor assembly acting against the spring, which is experimentally equated to the amount of drag force on the rotor assembly. The drag force is proportional to the fluid density of the two-phase mixture multiplied by fluid velocity squared. From these two measurements the fluid density of the two-phase mixture is calculated. By utilizing the rotor assembly as the drag body the shadowing problem which is experienced in the prior art is eliminated.

It is an object of the present invention to measure the density of a two-phase mixture flowing through a tubular member.

It is a further object of the present invention to measure the fluid density of a two-phase mixture flowing through a tubular member by measuring the rotational speed of a rotor assembly axially disposed within the tubular member and by measuring the drag forces exerted upon the rotor assembly.

BRIEF DESCRIPTION OF THE DRAWINGS

Other objects, features, and advantages of the present invention will become more fully apparent from the following detailed description of the preferred embodiment, the appended claims and the accompanying drawings in which:

FIG. 1 is a sectional view of the device for measuring the fluid density of a two-phase mixture;

FIG. 2 is a side view taken along lines 2—2 in FIG. 1;

DETAILED DESCRIPTION OF THE PREFERRED EMBODIMENT

Figure 3:
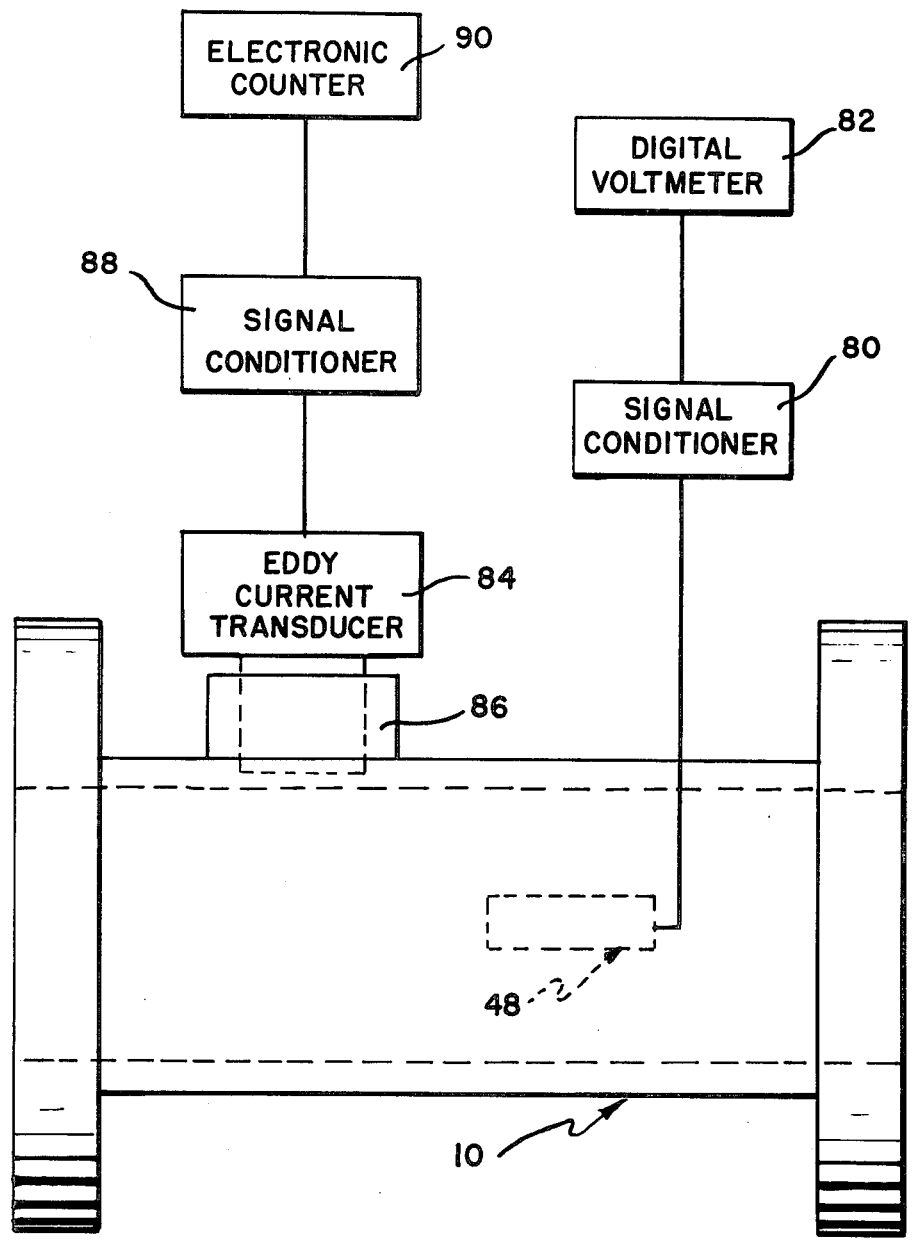
FIG. 3 is a schematic diagram of the device for measuring the fluid density of a two-phase mixture.

The preferred embodiment of the present invention is illustrated by way of example in FIGS. 1-3. With specific reference to FIGS. 1 and 2, right circular cylindrical tubular member 10 has an upstream side 12 and a downstream side 14. This embodiment of the invention is designed only to measure the fluid density of a two-phase mixture flowing from upstream side 12 to downstream side 14. By slight modification of the design described hereinafter, it could be made to measure two-phase flow in two directions. Integrally attached to either end of tubular member 10 are end flanges 15 which are provided for attaching tubular member 10 to external pipes.

Axially disposed within the hollow center of tubular member 10 is rotor assembly 16. Rotor assembly 16 has six blades 18 uniformly spaced about central hub 20. Blades 18 are all identical in shape and each extend to a point very close to the inside edge of tubular member 10 to insure that a majority of the two-phase mixture which flows through tubular member 10 comes in contact with blades 18. Since rotor assembly 16 is used as a drag body, the shape and number of blades 18 can be adjusted to obtain the desired drag features. These desired drag features depend upon the anticipated condition of the two-phase mixture which flows through tubular member 10. Rotor assembly 16 also comprises graphite bushing 22 which is lightly pressed into hub 20 and stainless steel shaft 24 which is pressed into bushing 22.

Rotor assembly 16 is supported within the center cavity of tubular member 10 as follows. Disposed axially on the upstream side of rotor assembly 16 is right circular cylindrical tubular support 26. Support 26 is supported axially within the center cavity of tubular member 10 by four identical rectangular fins 28. Fins 28 are evenly spaced about and extend along the entire length of support 26. Fins 28 are integrally attached to the inner surface of tubular member 10 and the outer surface of support 26 so that the end face of support 26 is coplanar with the upstream side end face of tubular member 10.

Disposed axially on the downstream side of rotor assembly 16 is right circular cylindrical tubular support 30. Support 30 is supported axially within the center cavity of tubular member 10 by four rectangular fins 32 in a similar fashion as is support 26 so that the end face of support 30 is coplanar with the downstream side end face of tubular member 10. Fins 28 and 32 also function as flow straightener blades. The number of fins 28 or 32 is not critical in the preferred embodiment.

Mounted on the upstream end of support 26 is end cap 34. End cap 34 comprises rounded cone-shaped member 36 with shaft 38 protruding from its base. Shaft 38 is press fit into the hollow center of support 26 so that cone-shaped member 36 protrudes from the center cavity of tubular member 10. The outer surfaces of cone-shaped member 36 and support 26 line up at the point at which they mate to form a continuous surface. Mounted on the downstream end of support 30 is end cap 40. End cap 40 comprises rounded cone-shaped member 42 mounted upon shaft 43 which are identical in shape to cone-shaped member 36 and shaft 38 except downstream end cap 40 has a hollow center which will be explained later. Shaft 43 is press fit into the hollow center of support 30 so that cone-shaped member 42 protrudes from the center cavity of tubular member 10. The outer surfaces of cone-shaped member 42 and support 30 line up at the point at which they mate to form a continuous surface. End cap 34 and end cap 40 act as flow streamliners which are provided to reduce the drag and minimize disruption of flow through tubular member 10.

Press fit into the hollow centers of the downstream side of support 28 and the upstream side of support 30 are sleeve bearings 44. Shaft 24 is rotatably mounted within bearings 44 such that rotor assembly 16 is disposed between support 26 and support 30 and is allowed to freely rotate perpendicularly about the axis of tubular member 10. Bearings 44 are also spaced far enough apart so that rotor assembly 16 can move axially within bearings 44. This will be discussed in more detail later.

It is noted that the design of upstream flow straightener assembly 45 which includes support 26, fin 28 and end cap 34, and of downstream flow straightener assembly 46 which includes support 30, fins 32 and end cap 40 serve not only to support rotor assembly 16 within the center cavity of tubular member 10, but also to reduce as much as possible the rotational component of the two-phase mixture which flows through tubular member 10. This allows a more accurate measurement of two-phase flow.

A conventional commercially available Linear Variable Differential Transformer (LVDT) assembly 48 is disposed within the hollow right circular cylindrical center of support 30. LVDT assembly 48 is provided to measure the axial movement of shaft 24. Although an LVDT is used in the preferred embodiment to measure the linear movement of shaft 24, other devices which are well known to those of ordinary skill in the art may also be utilized. The LVDT is used in the preferred embodiment because it has a very high resolution for small changes in linear movement.

LVDT assembly 48 comprises LVDT case 50 which is securely positioned within a center portion of the hollow center of support 30 by a set screw not shown in the figures. Slidably disposed within the hollow center of LVDT case 50 is LVDT core 52. LVDT core 52 is threaded onto stems 54 and 55 which extend out either end of LVDT case 50. Stems 54 and 55 ride in jewelled bearings 56 and 57 which are supported by guides 58 and 60 at either end of LVDT case 50. The downstream end face of guide 60 butts up against the distal end face of shaft 43 of end cap 40. LVDT core 52 is centered in LVDT case 50 coaxial to tubular member 10 by two identical compression springs 62 and 64. Spring 64 is captured between guide 60 and spring retention nut 66 which is screwed onto threaded distal portion 68 of stem 55. Spring 62 is captured between guide 58 and thrust piston 70 which is screwed onto threaded distal portion 72 of stem 54.

Face 74 of thrust piston 70 which is perpendicular to the axis of tubular member 10 comes in contact with the downstream end, end 75, of shaft 24. End 75 of shaft 24 is rounded to reduce rotational friction between it and thrust piston 70. Flat bearing surface insert 76 is integrally embedded in thrust piston 70 at the point in which end 75 of shaft 24 contacts thrust piston 70. Bearing surface insert 76 can be made from a hard material such as carbide or diamond. Bearing surface insert 76 and end 75 of shaft 24 are utilized because it has been determined that more accurate measurements of two-phase flow can be realized by minimizing frictional forces in axially moving parts.

Springs 62 and 64 serve two functions. As noted before, they center LVDT core 52 within the center of LVDT case 50. They also provide a spring force which reacts against rotor assembly 16. With no flow through tubular member 10, shaft 24 rests loosely within bearings 44 exerting no force on LVDT assembly 48 through thrust piston 70. When a two-phase mixture flows through tubular member 10 and contacts blades 18, rotor assembly 16 is forced to rotate about the axis of shaft 24. This causes an axial force in shaft 24 which in turn causes shaft 24 to come in contact with thrust piston 70 and thereby interact with springs 62 and 64. LVDT assembly 48 measures the linear displacement of LVDT core 52 and thereby the linear displacement of rotor assembly 16. The linear displacement of LVDT core 52 is proportional to the spring forces that balance the fluid forces acting on rotor assembly 16. The linear displacement of LVDT core 52 acting against springs 62 and 64 can be experimentally equated to the amount of drag on rotor assembly 10. This is proportional to the fluid density of the two-phase mixture multiplied by fluid velocity squared.

It is noted that the axial motion of rotor assembly 16 is limited by the space between hub 20 and bearings 44. The equilibrium position of thrust piston 70 is adjusted so that with no flow rotor assembly 16 can freely rotate in bearings 44. The compression of the springs and the space between hub 20 and bearings 44 is also adjusted so that when the maximum anticipated flow occurs (1) hub 20 does not come in contact with bearings 44 and therefore rotor assembly 16 can freely rotate about the axis of tubular member 10, and (2) the total range of movement of thrust piston 70 and thereby LVDT core 52 is within the linear range of output voltage for LVDT assembly 48. Also, both springs 62 and 64 remain in compression throughout the maximum axial motion of rotor assembly 16. This will be discussed in more detail shortly.

The compression of springs 62 and 64 is adjusted as follows. Threaded portion 68 of stem 55 extends out of the hollow center of support 30. The end cap has a hollow center within which threaded portion 68 of stem 55 is disposed. To adjust the compression of springs 62 and 64 end cap 40 is removed, a screwdriver is inserted into slot 78 at the end of stem 55 to prevent stem 55 from rotating, and spring retention nut 66 is positioned at various points along stem 55 by rotating it, thus changing the compression of springs 62 and 64.

LVDT assembly 48 is a mutual inductance element which produces a voltage output proportional to the displacement of LVDT core 52 and which operates as follows. Although not visible in the figure, AC carrier excitation is applied to a primary coil. Two identical secondary coils, symmetrically spaced about the primary, are connected externally in a series-opposing circuit. Movement of the non-contacting magnetic LVDT core 52 by thrust piston 70 and shaft 24 varies the mutual inductance of each secondary coil to the primary coil. This change in mutual inductance determines the voltage induced from the primary coil to each secondary coil.

If LVDT core 52 is centered between the secondary windings, the voltage induced in each secondary is identical and 180° out-of-phase, so there is no net output. If LVDT core 52 is moved off center, the mutual inductance of the primary with one secondary will be greater than with the other, and a differential voltage will appear across the secondaries in series. For small off-center displacements, this voltage is a linear function of displacement.

Because there is no physical contact between LVDT core 52 and the coil, the only sliding friction in the assembly is between stems 54 and 56 and their jewel bearings 58 and 60. The small mass of LVDT core 52 and stems 54 and 56 enhance capabilities of rapid response for making dynamic measurements.

Referring to FIG. 3 the LVDT readout is obtained with signal conditioner 80 and digital voltmeter 82 which are both well known in the art. Signal conditioner 80 supplies the AC input to LVDT assembly 48 and also converts the differential output of LVDT assembly 48 to a DC output. Digital voltmeter 82 is connected directly to the DC output of signal conditioner 80.

Eddy current transducer 84 which is well known in the art is provided to measure the rotational velocity of rotor assembly 10. Referring to FIG. 1, transducer 84 is screwed into the side of tubular member 10 through a threaded hole 85 which extends through to the interior of tubular member 12 at a point where rotor assembly 16 is located. The part of transducer 84 outside of the tubular member 10 is encased in boss 86 which is securely attached to the outer surface of tubular member 10 and serves to protect transducer 84.

Transducer 84 operates as follows. As the tips of blades 18 pass transducer 84, a train of irregular shaped pulses, at a frequency proportional to rotor speed are produced in transducer 84. Referring to FIG. 3 these pulses are routed to signal conditioner 88 which changes them to square wave pulses. The square wave pulses are routed to electronic counter 90. Both signal conditioner 80 and electronic counter 90 are well known in the art. The counter readings from counter 90 can readily be converted to revolutions per minute. The rotor speed is directly proportional to the velocity of two-phase mixture flowing through tubular member 10. It is noted that there are several devices well known in the art which could be substituted for transducer 84 to measure the rotor speed.

The fluid density, or two-phase flow, of the two-phase mixture is calculated as follows. The rotational speed of rotor assembly 16 as measured by transducer 84 is directly proportional to the velocity (V) of the two-phased mixture. The drag forces exerted on rotor assembly 16 as measured by LVDT assembly 48 are proportional to the fluid density (d) of the two-phase mixture multiplied by fluid velocity squared ($V^2$). Therefore fluid density is determined with the following formula:

$$d = (dV^2)/V^2.$$

By utilizing the device as described above to measure the fluid density of a two-phase mixture, the shadowing problem which is experienced with the prior art is eliminated.

While the present invention has been disclosed in connection with the preferred embodiment thereof, it should be understood that there may be other embodiments which fall within the scope and spirit of the invention as defined by the following claims.

The embodiments of the invention in which an exclusive property or privilege is claimed are defined as follows:

1. A device for measuring the fluid density of a two-phase mixture flowing through a tubular member comprising:

a rotor assembly axially disposed within the tubular member;

means for rotatively supporting the rotor assembly within the tubular member, the support means permitting the rotor assembly to move axially within the tubular member;

means for measuring relative axial movement of the rotor assembly;

means for measuring the rotational speed of the rotor assembly, said rotational speed being directly proportional to the fluid velocity; and a pair of springs exerting force in the opposite direction upon the rotor assembly, thereby balancing the rotor assembly against the pair of springs, linear displacement of the rotor assembly being proportional to the spring forces that balance the fluid forces acting on the rotor assembly, said linear displacement being experimentally equatable to the amount of rotor assembly drag force which is proportional to the fluid density (d) of the mixture multiplied by fluid velocity squared ($V^2$), fluid density accordingly being derivable from the formula $$d = (d(V)^2)/V^2$$

where d = fluid density and V = fluid velocity.

2. The device of claim 1 wherein the rotor assembly comprises:

a shaft axially disposed within the tubular member; and a plurality of blades mounted upon the shaft for joint rotation about the axis of the tubular member.

3. The device of claim 2 which further comprises flow straightening means for reducing the rotational component of the flow of the two-phase mixture as it moves through the tubular member and contacts the plurality of blades of the rotor assembly.

4. The device of claim 3 wherein the flow straightener means comprise:

a first support axially disposed on one side of the rotor assembly which has a uniformly shaped outer surface along its length;

a second support axially disposed on the other side of the rotor assembly which has a uniformly spaced outer surface along its length;

a first plurality of planar fins spaced about and extending along the length of the first support and attached to an outside surface of the first support and to an inside surface of the tubular member; and a second plurality of planar fins spaced about and extending along the length of the second support and attached to an outside surface of the support and to the inside surface of the tubular member.

5. The device of claim 4 wherein the flow straightener further comprises:

a first cone-shaped cap secured to an outer end of the first support; and a second cone-shaped cap secured to an outer end of the second support.

6. The device of claim 5 wherein the means for rotatively supporting comprise:

a first bearing attached to an inner end of the first support; and a second bearing attached to an inner end of the second support, and wherein the shaft is rotatively mounted within the first and second bearings.

7. The device of claim 6 wherein the means for measuring the rotational speed of the rotor assembly is an eddy current transducer mounted to the tubular member.

8. A device for measuring fluid density of a two-phase mixture flowing from an upstream side to a downstream side of a tubular member comprising:

a rotor assembly axially disposed within the tubular member;

means for rotatively supporting the rotor assembly within the tubular member, the support means permitting the rotor assembly to move axially within the tubular member;

means for measuring relative axial movement of the rotor assembly;

means for measuring the rotational speed of the rotor assembly which is directly proportional to the fluid velocity; and a spring which is axially loaded against the downstream end of the rotor assembly, linear displacement of the rotor assembly being proportional to the spring forces that balance the fluid forces acting on the rotor assembly, said linear displacement being experimentally equatable to the amount of rotor assembly drag force which is proportional to the fluid density (d) of the mixture multiplied by fluid velocity squared ($V^2$), fluid density accordingly being derivable from the formula $$d = (d(V)^2)/V^2$$

where d=fluid density and V=fluid velocity.

9. The device of claim 8 wherein the rotor assembly comprises:

a shaft axially disposed within the tubular member; and a plurality of blades mounted upon the shaft for joint rotation about the axis of the tubular member.

10. The device of claim 9 which further comprises flow straightening means for reducing the rotational component of the flow of the two-phase mixture as it moves through the tubular member and contacts the plurality of blades of the rotor assembly.

11. The device of claim 10 wherein the flow straightening means comprise:

a first support axially disposed on the upstream side of the rotor assembly which has a uniformly shaped outer surface along its length;

a second support axially disposed on the downstream side of the rotor assembly which has a uniformly shaped outer surface along its length;

a first plurality of planar fins spaced about and extending along the length of the first support and attached to an outside surface of the first support and to an inside surface of the tubular member; and a second plurality of planar fins spaced about and extending along the length of the second support and attached to an outside surface of the second support and to the inside surface of the tubular member.

12. The device of claim 11 wherein the flow straightener further comprises:

a first cone-shaped cap secured to an upstream end of the first support; and a second cone-shaped cap secured to a downstream end of the second support.

13. The device of claim 12 wherein the means for rotatively supporting comprise:

a first bearing attached to a downstream end of the first support; and a second bearing attached to an upstream end of the second support, and wherein the shaft is rotatively mounted within the first and second bearings.

14. The device of claim 13 wherein the means for measuring the relative axial movement of the rotor assembly comprises a linear variable differential transformer which is disposed within a hollow center of the second support and comes in contact with one end of the shaft.

15. The device of claim 14 wherein the means for measuring the rotational speed of the rotor assembly is an eddy current transducer mounted to the tubular member.

* * * * *